United States Patent [19]

Sakurai et al.

[11] 4,411,647
[45] Oct. 25, 1983

[54] TAMPON APPLICATOR

[75] Inventors: Akira Sakurai, Utsunomiya; Takashi Nakanishi, Mashikomachi; Akio Nishimura, Ichikaimachi, all of Japan

[73] Assignee: Kao Soap Co., Ltd., Tokyo, Japan

[21] Appl. No.: 290,048

[22] Filed: Aug. 5, 1981

[30] Foreign Application Priority Data

Aug. 11, 1980 [JP] Japan ............... 55-110040

[51] Int. Cl.³ ............................................. A61F 13/20
[52] U.S. Cl. ........................................ 604/16; 604/18
[58] Field of Search ............. 128/225, 263, 285, 264, 128/270, 130; 604/11, 15, 16, 18, 218; 401/176, 401/179

[56] References Cited
U.S. PATENT DOCUMENTS 3,749,094  7/1973  Duncan ........................... 604/15
4,048,998  9/1977  Nigro ............................. 128/263

FOREIGN PATENT DOCUMENTS 2033754  5/1980  United Kingdom ............... 604/15

Primary Examiner—Richard J. Apley
Assistant Examiner—T. J. Wallen
Attorney, Agent, or Firm—Flynn, Thiel, Boutell & Tanis

[57] ABSTRACT

A tampon applicator comprises an outer cylinder containing an absorber and first and second inner cylinders for pushing out the absorber, wherein the first inner cylinder is fitted slidably into the outer cylinder, the second inner cylinder is fitted slidably into the first inner cylinder, and the second inner cylinder is provided on the outer surface thereof with a projection(s) having means for significantly changing the size thereof in the radial direction, which projection(s) is(are) kept in the first inner cylinder before use but serve to transmit a pushing-out pressure to the first inner cylinder at the time of the application.

9 Claims, 15 Drawing Figures

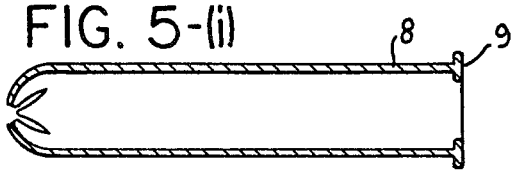 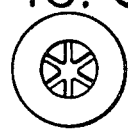
FIG. 5-(i)  FIG. 6-(i)
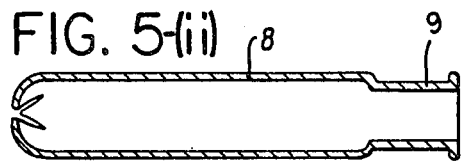 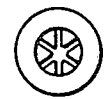
FIG. 5-(ii)  FIG. 6-(ii)
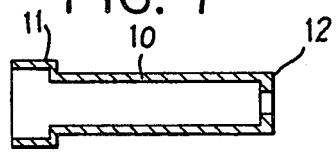
FIG. 7
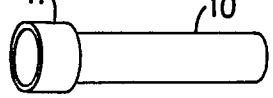
FIG. 8
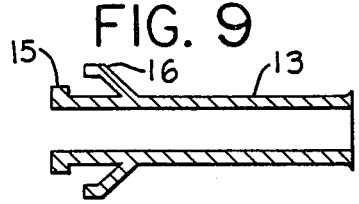
FIG. 9
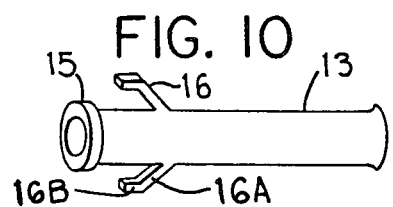
FIG. 10

TAMPON APPLICATOR

The present invention relates to an article for the treatment of menstrual excretions. Particularly, the present invention relates to a tampon provided with an applicator which affords a great advantage for the users.

Recently, the use of menstruation tampons has been increasing in place of napkins for various reasons. The napkins cannot be used by users wearing clothes of a special design which does not admit the bulkiness of the napkin, while such a care is unnecessary in the case of the tampons. For further utilizing such an advantage of tampons, ideas for developing a tampon small in size and handy to carry which can be inserted easily and precisely in the body will be necessitated. Currently, tampons of various types as will be shown below are available on the market.

A first type of tampons are those wherein a tampon absorber is to be taken out from a bag at the time of use and to be inserted into the body by fingers or by means of a paper stick. They are called finger type tampons and stick type tampons, respectively.

However, the tampons of those types cannot be inserted in the body without directly touching the same by fingers. This fact poses hygienic problems. In addition, the precise adjustment of the position is difficult at the time of the insertion.

A second type of tampons are those of applicator type which are to be inserted into the body by extrusion from an inserting means comprising an outer cylinder and a freely slidable inner cylinder. A tampon absorber is extruded through an opening at an end of the outer cylinder and into the body by means of the inner cylinder. In tampons of this second type, the hygienic problems posed by the tampons of the first types are solved. Further, in the insertion, the absorber can be inserted in a suitable depth in the body using the inserting means and, therefore, a feeling of physical disorder unavoidable in the first type tampons can be greatly reduced.

The present invention relates to an improvement in or relating to an applicator for the menstruation tampon of the second type having such a mechanism that the tampon absorber is to be inserted by an inserting means.

There have been proposed various tampons of the second type (applicator type). Typical examples of them will be illustrated with reference to the drawings.

As materials of the applicators, those made of paper have been put on the market in the prior art and brought about great advantages for the users as described above.

BRIEF DESCRIPTION OF DRAWINGS

FIGS. 5-(i) and 5-(ii) are longitudinal sections showing two embodiments of the outer cylinder of the applicator of the present invention. FIGS. 6-(i) and 6-(ii) are end views of the tail side of the outer cylinders shown in FIGS. 5-(i) and 5-(ii), respectively. FIG. 7 is a longitudinal section showing an embodiment of the first cylinder of the applicator of the present invention. FIG. 8 is a perspective view thereof. FIGS. 9 and 10 are a longitudinal section and perspective view, respectively, showing an embodiment of the second inner cylinder of the applicator of the present invention.

Figure 1:
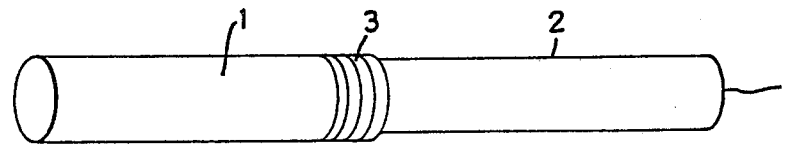
FIG. 1 is a perspective view and FIG. 2 is a longitudinal section, respectively, of a conventional tampon of the paper applicator type.

In the figures, reference numeral 8 designates an outer cylinder, 10 a first inner cylinder, 13 a second inner cylinder, 9 a tail for preventing the slipping-out of the outer cylinder, 11 a tip for preventing the slipping out of the first inner cylinder, 12 a tail for preventing the slipping-out of the first inner cylinder, 15 a tip for preventing the slipping-out of the second inner cylinder, 16 a protection for moving the first inner cylinder, and 14 an absorber.

DISCUSSION OF THE PRIOR ART

Figure 2:
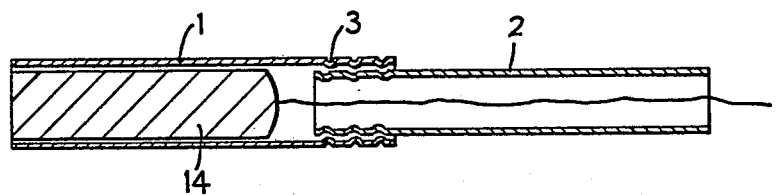

FIG. 1 is a perspective view and FIG. 2 shows a longitudinal section of a conventional applicator. At the time of use of this applicator, an outer cylinder 1 is inserted in the body and then an inner cylinder 2 is slid towards the inside of the body to extrude an absorber 14 therein, thereby completing the insertion. Some of the applicators of this type are provided with circumferential grooves 3 so as to prevent the inner cylinder from slipping out. However, the grooves are not a satisfactory means for the prevention of this trouble. Under the circumstances as above, there have been problems left unsolved such as the slipping-out of the inner cylinder from the outer cylinder to make the applicator no more useful and a high bulkiness (the whole length of the applicator is about 3 times as long as the tampon absorber) which makes it inconvenient to carry.

Figure 3:
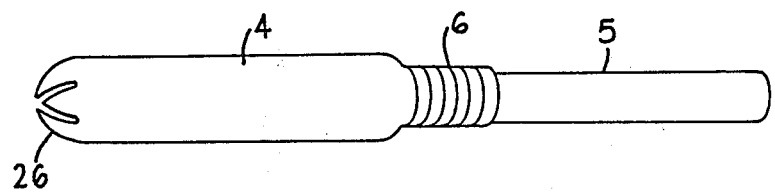
FIG. 3 is a perspective view and FIG. 4 is a longitudinal section, respectively, of a conventional tampon of the plastic applicator type.
Figure 4:
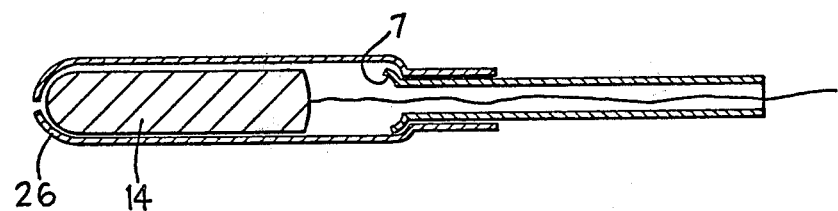

Following the paper applicators, plastic applicators have been put on the market. FIG. 3 is a perspective view and FIG. 4 is a section thereof. The applicator of this type comprises an outer cylinder 4 and a cylinder 5 having an end 7 for preventing the slipping-off thereof from the outer cylinder 4. The outer cylinder 4 is shaped so that petalous projections 26 are provided at an end thereof. The petalous projections 26 form a hemisphere which retains the absorber 14. In the cylinder 4, a tail 6 has a diameter slightly smaller than that of the body thereof. In the applicator of this type, the problem of bulkiness which makes the applicator not handy to carry has not been solved yet, though the problem of slipping-off has substantially been solved.

SUMMARY OF THE INVENTION

After intensive investigations made for the purpose of solving the above problems, the inventors have attained the present invention.

An object of the present invention is to provide a sanitary tampon in which an absorber can be extruded from an applicator precisely and which is smaller in size and handy to carry. Another object of the present invention is to provide a tampon applicator having such a structure that the inner cylinder is prevented from slipping-out.

The present invention relates to a tampon applicator comprising an outer cylinder containing an absorber and first and second inner cylinders for extruding the absorber, wherein the first inner cylinder is fitted slidably into the outer cylinder, the second inner cylinder is fitted slidably into the first inner cylinder, and the second inner cylinder is provided on its outer surface with projection(s) having means for significantly changing the size thereof in the radial direction, which projection(s) is(are) kept in the first inner cylinder before use but serve to generate an extruding pressure in the first inner cylinder at the time of the application.

DETAILED DESCRIPTION

The present invention will be illustrated in more detail with reference to figures showing embodiments of the invention.

Figure 11:
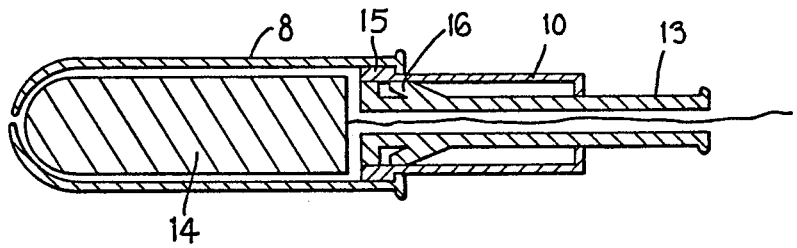
FIG. 11 is a longitudinal section showing a tampon containing the applicator of the present invention before use.
Figure 12:
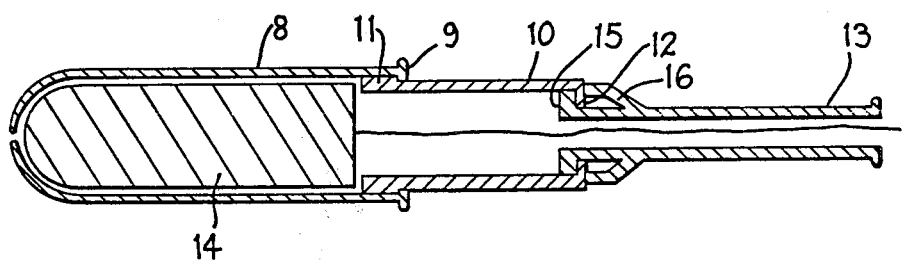
FIG. 12 is a longitudinal section showing the same immediately before insertion and FIG. 13 is a longitudinal section showing the same after the insertion.
Figure 13:
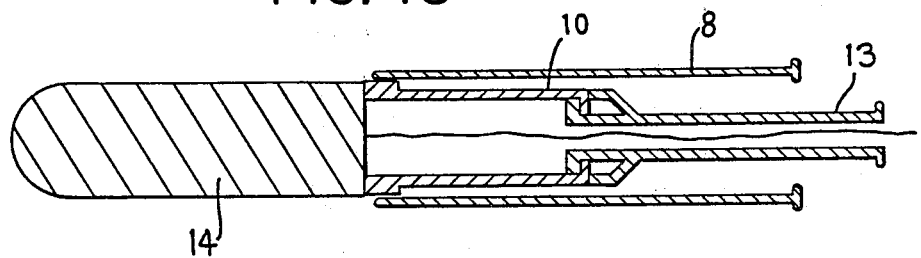

FIG. 5-(i) and 5-(ii) are longitudinal sections showing outer cylinders of applicators constituting the tampons of the present invention. FIGS. 6-(i) and 6-(ii) are side perspective views of the cylinders of FIGS. 5-(i) and 5-(ii) viewed from the tail side. FIG. 7 is a longitudinal section showing an embodiment of the first inner cylinder of the applicator of the present invention. FIG. 8 is a perspective view of the first inner cylinder. FIG. 9 is a longitudinal section showing an embodiment of the second inner cylinder of the applicator of the invention. FIG. 10 is a perspective view of the second inner cylinder. FIGS. 11, 12 and 13 show the arrangements of the outer cylinder, first inner cylinder, second inner cylinder and absorber of the tampon of the invention, FIG. 11 being a longitudinal section showing the arrangement before use, FIG. 12 being a longitudinal section showing the arrangement immediately before the insertion of the absorber and FIG. 13 being a profile showing the insertion of the absorber into the vagina.

An outer cylinder 8 of the applicator according to the present invention has a substantially cylindrical shape as shown in FIGS. 5-(i) and 5-(ii) and has at the tail a part 9 having an inner diameter smaller than that of the body thereof. The inner cylinders comprise the first and the second inner cylinders. The first inner cylinder 10 has a body having an outer diameter substantially equal to or slightly smaller than the inner diameter of said part 9 of the outer cylinder as shown in FIGS. 7 and 8. The first inner cylinder 10 has (1) a part 11 having an outer diameter substantially equal to or slightly smaller than the inner diameter of the body of the outer cylinder but larger than the inner diameter of the part or inwardly extending flange 9 of the outer cylinder at the tip thereof and (2) a part 12 having an inner diameter smaller than the inner diameter of the body thereof at the tail.

On the other hand, the second inner cylinder 13 has a shape as shown in FIGS. 9 and 10. It has a body having an outer diameter substantially equal to or slightly smaller than the inner diameter of the part 12 of the first inner cylinder 10. The second inner cylinder 13 has also a part or outwardly extending flange 15 having an outer diameter substantially equal to or slightly smaller than the inner diameter of the body of the first inner cylinder 10 but larger than the inner diameter of the part 12 of the first cylinder at the tip thereof. Behind the part 15, at least one bent projection 16 is provided. The projection can be deformed towards the body of the second inner cylinder 13 by virtue of its elasticity and also it can be pressed in the first inner cylinder. Therefore, it is so designed that when it is forcedly bent towards the body to the maximum degree, the difference in level between the part 15 and the body is a little larger than the radial height of the projection. At this moment, the projection 16 has such a thickness or height that the second inner cylinder can be passed through the tail part 12 of the first inner cylinder.

As shown in FIG. 10, each projection 16 includes a first section 16A which extends radially outwardly and is inclined toward the end of the cylinder 13 having the part 15, and includes a second section 16B which extends toward the part 15 from the outer end of the section 16A generally parallel to the cylinder 13.

In the tampon applicator of the present invention, the outer cylinder 8, the first inner cylinder 10, the second inner cylinder 13 and absorber 14 are arranged as shown in FIG. 11 before use. More particularly, the absorber 14 is kept in the tip part of the outer cylinder. Behind the absorber 14, the second inner cylinder 13 is arranged in the first inner cylinder 10. This combination is positioned in the outer cylinder. In this case, the elastic, bent projection 16 for the extrusion of the first inner cylinder is hidden in the first inner cylinder and pressed against the body of the second inner cylinder 13 by the inner diameter of the body of the first inner cylinder 10.

In using the applicator, a part of the outer cylinder 8 is held and the tail of the second inner cylinder 13 is slid backward rightwardly as shown in FIG. 12. At this moment, the tip 11 of the first inner cylinder 10 is fixed and engaged with the tail 9 of the outer cylinder and the elastic projection 16 of the second inner cylinder 13, i.e. the bend 16 for the extrusion of the first inner cylinder, slides along the inner wall of the first inner cylinder 10 towards the outside through the tail 12 of the first inner cylinder. Consequently, the projection is released from the compression and, therefore, from the deformation and engages the tail of the first inner cylinder. The second inner cylinder 13 is fixed when the part 12 of the first inner cylinder is fitted to the tip 15 thereof (FIG. 12).

Thereafter, as shown in FIG. 13, the outer cylinder 8 is inserted into the body and the tail of the second inner cylinder is slid towards the inside of the body, whereby the extruding bend 10 of the second inner cylinder 13 presses the tail of the first inner cylinder 10. As a result, the absorber 14 is extruded into the vagina through the tip of the outer cylinder 8 to complete the insertion.

The material of the tampon applicator of the present invention is not particularly restricted. However, the deformable and restorable properties are required of the bend 16 for the extrusion of the inner cylinder. Therefore, it is made of an elastic material such as polyethylene or polypropylene. Other projections provided with means of changing their size in the radial direction are also usable.

The tampon provided with the applicator of the present invention can easily be produced by inserting a combination of the first and the second inner cylinders in the outer cylinder 8 through the tip thereof, then placing the absorber therein and, if necessary, curving the tip wall of the outer cylinder to form a hemisphere.

Thus obtained, the tampon of the present invention can be stored under good hygienic conditions before use. The inner cylinders will not slip out from the outer cylinder during the carrying. The size of this tampon is far smaller than those of the conventional products and it is handy to carry. It is ready for use merely by the simple operation of sliding the inner cylinders. Therefore, according to the present invention, the defect of the conventional tampons of the applicator type, i.e. the high bulkiness which has been incompatible with the improved feeling during the use thereof, can remarkably be overcome and the essential advantage of the tampon, i.e. the smallness in size as compared with the napkin, can be provided for the user.

The embodiments of the invention in which an exclusive property or privilege is claimed are defined as follows:

1. A tampon applicator, comprising: an outer cylinder having a front end and a rear end; a tampon contained in said outer cylinder and adapted to be pushed out of the front end of said outer cylinder; pushing means for pushing said tampon out of the front end of said outer cylinder, said pushing means comprising a first inner cylinder mounted for lengthwise sliding movement within said outer cylinder and having a front end and a rear end, the front end of said first inner cylinder being adapted to engage the rearward end of said tampon to push same out of said outer cylinder when said first inner cylinder is pushed forwardly in said outer cylinder, said first inner cylinder having laterally extending wall means longitudinally spaced from the front end thereof, and a second inner cylinder mounted for lengthwise sliding movement within said first inner cylinder and being movable independently of said outer cylinder, said second, inner cylinder having at least one projection received within said first inner cylinder and extending outwardly from the external wall of said second inner cylinder toward the internal wall of said first inner cylinder, said projection being movable past said wall means when said second inner cylinder is moved toward the rear end of said first inner cylinder and then being engageable with the rearward side of said wall means so that subsequent forward movement of said second inner cylinder will move said first inner cylinder forwardly in said outer cylinder.

2. A tampon applicator as claimed in claim 1, in which said projection is elastically deformable in a lateral direction with respect to the remainder of said second inner cylinder and with respect to said wall means.

3. A tampon applicator as claimed in claim 2, wherein said first inner cylinder has a forward part having a first inner diameter and a rearward part having a second inner diameter which is smaller than said first inner diameter, said second inner cylinder has a forward part having a first outer diameter and a rearward part having a second outer diameter smaller than said first outer diameter, said second inner diameter of said firs inner cylinder being smaller than said first outer diameter of said second inner cylinder and larger than said second outer diameter of said second inner cylinder, said rearward part of said first inner cylinder being engageable with said forward part of said second inner cylinder to limit relative movement of said second inner cylinder in the rearward direction relative to said first inner cylinder.

4. A tampon applicator as claimed in claim 2, wherein said outer cylinder has a forward part having a first inner diameter and a rearward part having a second inner diameter smaller than said first inner diameter, and said first inner cylinder has a forward part having a first outer diameter and a rearward part having a second outer diameter smaller than said first outer diameter, said second inner diameter of said outer cylinder being smaller than said first outer diameter of said first inner cylinder and larger than said second outer diameter of said first inner cylinder, said rearward part of said outer cylinder being engageable with said forward part of said first inner cylinder to limit relative movement of said first inner cylinder in the rearward direction relative to said outer cylinder.

5. A tampon applicator as claimed in claim 1 or claim 4, in which said second inner cylinder has two of said projections extending outwardly therefrom on diametrically opposite sides thereof.

6. A tampon inserter, comprising an elongated outer tube having a forward end and a rearward end, said outer tube containing a tampon; an elongated inner tube having a forward end and a rearward end, said inner tube being slidably supported in said outer tube for movement relative thereto between a first retracted position in which the forward end of said inner tube is adjacent to the rearward end of said outer tube and a second insertion position in which said forward end of said inner tube is within said outer tube and is close to the forward end thereof whereby to move said tampon out of said outer tube through the forward end thereof; an elongated inner member having a forward end and a rearward end, said inner member being slidably supported in said inner tube for movement relative thereto independently of said outer tube between a third position in which the forward end of said inner member is located close to the forward end of said inner tube and a fourth position in which the forward end of said inner member is located close to the rearward end of said inner tube, and means for releasably locking said inner tube and said inner member in said fourth position.

7. The tampon inserter of claim 6, wherein said means for releasably locking said inner tube and inner member in said fourth position includes an inwardly projecting flange adjacent to said rearward end of said inner tube, an outwardly projecting flange adjacent to the forward end of said inner member, said flange on said inner member engaging said flange on said inner tube in said fourth position to prevent movement thereof past said fourth position, and at least one elastic, outwardly projecting, inwardly deflectable projection on said inner member adjacent said flange thereon, said projection being deflected inwardly by said flange on said inner tube as said inner member is moved from said third position to said fourth position relative to said inner tube and then being moved outwardly by its elasticity when said inner member and inner tube reach said fourth position so that said flange on said inner tube is disposed between said projection and said flange on said inner member in said fourth position, whereby said inner tube and said inner member are releasably locked in said fourth position.

8. The tampon inserter of claim 7, wherein said projection is elongated and includes a first section extending outwardly from said inner member and inclined toward said forward end of said inner member and a second section extending from the outer end of said first section toward said forward end of said inner member.

9. The tampon inserter of claim 8, including two said projections on said inner member.

* * * * *